(12) United States Patent
Eckel et al.

(10) Patent No.: US 10,240,959 B2
(45) Date of Patent: Mar. 26, 2019

(54) DEVICES, SYSTEMS, AND METHODS FOR VOLUMETRICALLY MEASURING SYRINGE FLUID

(71) Applicant: The University of North Carolina at Chapel Hill, Chapel Hill, NC (US)

(72) Inventors: Stephen Eckel, Chapel Hill, NC (US); Christopher Roberts, Durham, NC (US); Chase Dubois, Carrboro, NC (US); Jorge Martínez-Blat, Carrboro, NC (US); John C. Pamplin, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 315 days.

(21) Appl. No.: 15/343,865

(22) Filed: Nov. 4, 2016

(65) Prior Publication Data

US 2017/0146381 A1 May 25, 2017

Related U.S. Application Data

(63) Continuation of application No. PCT/US2015/029488, filed on May 6, 2015.
(Continued)

(51) Int. Cl.
*G01F 11/02* (2006.01)
*G06F 19/00* (2018.01)
(Continued)

(52) U.S. Cl.
CPC ........... *G01F 11/027* (2013.01); *A61J 1/2096* (2013.01); *A61M 5/31533* (2013.01);
(Continued)

(58) Field of Classification Search
CPC . G01F 11/027; G01F 11/029; A61M 5/31535; A61M 5/31533;
(Continued)

(56) References Cited

U.S. PATENT DOCUMENTS

| | | | |
|---|---|---|---|
| 5,533,981 A * | 7/1996 | Mandro | A61M 5/1456 604/208 |
| 5,611,784 A | 3/1997 | Barresi et al. | |

(Continued)

FOREIGN PATENT DOCUMENTS

| | | |
|---|---|---|
| CN | 102266601 A | 12/2011 |
| EP | 2179758 A2 | 4/2010 |

(Continued)

OTHER PUBLICATIONS

Extended European Search Report for Application No. 15789369 dated Jan. 9, 2018.
(Continued)

Primary Examiner — Daniel S Larkin
Assistant Examiner — Anthony W Megna Fuentes
(74) Attorney, Agent, or Firm — Jenkins, Wilson, Taylor & Hunt, P.A.

(57) ABSTRACT

Devices, systems, and methods for volumetrically measuring syringe fluid are disclosed. In one aspect, a device for volumetrically measuring syringe fluid includes a reference plate, a flange adapter base attached at a first end of the reference plate for receiving a flange of a syringe, a plunger adapter disposed adjacent to a housing for receiving a plunger of the syringe, the plunger adapter being configured to slidingly move along a length of the reference plate, a displacement sensor disposed in the housing and configured to measure a displacement of the plunger adapter in relation to the flange adapter base as the plunger adapter is slid along the length of the reference plate, and a displacement con-
(Continued)

version mechanism disposed in the housing and configured to convert the displacement measurement of the plunger adapter to a volumetric measurement in order to determine a volume of fluid the syringe has drawn in.

24 Claims, 9 Drawing Sheets

Related U.S. Application Data

(60) Provisional application No. 61/988,972, filed on May 6, 2014.

(51) Int. Cl.
*A61J 1/20* (2006.01)
*A61M 5/315* (2006.01)
*A61M 5/31* (2006.01)
*A61M 5/178* (2006.01)

(52) U.S. Cl.
CPC ......... *A61M 5/31535* (2013.01); *G06F 19/00* (2013.01); *G06F 19/3468* (2013.01); *A61M 5/1782* (2013.01); *A61M 2005/3125* (2013.01); *A61M 2005/3126* (2013.01); *A61M 2005/31508* (2013.01); *A61M 2205/3306* (2013.01); *A61M 2205/3317* (2013.01); *A61M 2205/3375* (2013.01); *A61M 2205/3396* (2013.01); *A61M 2205/3584* (2013.01); *A61M 2205/50* (2013.01); *A61M 2205/502* (2013.01); *A61M 2205/52* (2013.01); *A61M 2205/70* (2013.01); *G01F 11/029* (2013.01)

(58) Field of Classification Search
CPC .. A61M 2205/3317; A61M 2005/3126; A61M 2205/502; A61M 2205/3584; A61M 2205/3375; A61M 2205/3396; A61M 2205/70; A61M 2205/3306; A61M 2205/52; A61M 5/1782; A61M 2005/3125; A61M 2005/31508; A61M 2205/50; A61J 1/2096; G06F 19/00; G06F 19/3468

See application file for complete search history.

(56) References Cited

U.S. PATENT DOCUMENTS

| | | | |
|---|---|---|---|
| 7,879,025 B2 | 2/2011 | Jacobson et al. | |
| 8,226,597 B2 * | 7/2012 | Jacobson | A61M 5/16886 604/151 |
| 8,231,566 B2 * | 7/2012 | Jacobson | A61M 5/16886 604/131 |
| 8,303,547 B2 * | 11/2012 | Brown | A61B 5/155 604/207 |
| 8,535,268 B2 | 9/2013 | Auld et al. | |
| 8,672,876 B2 * | 3/2014 | Jacobson | A61M 5/16886 604/151 |
| 8,672,886 B2 | 3/2014 | Smit et al. | |
| 2007/0112299 A1 * | 5/2007 | Smit | A61M 5/1456 604/67 |
| 2007/0260174 A1 * | 11/2007 | Jung | A61B 5/00 604/65 |
| 2011/0009812 A1 | 1/2011 | Brown | |

FOREIGN PATENT DOCUMENTS

| | | | |
|---|---|---|---|
| EP | 2327431 A1 | 6/2011 | |
| WO | WO 2005/102416 A1 | 11/2005 | |
| WO | WO 2006/130491 A2 | 12/2006 | |

OTHER PUBLICATIONS

European Notice of Publication for Application No. 15789369 dated Feb. 15, 2017.
International Search Report with Written Opinion for PCT Application No. PCT/US2015/029488 dated Sep. 17, 2015.

* cited by examiner

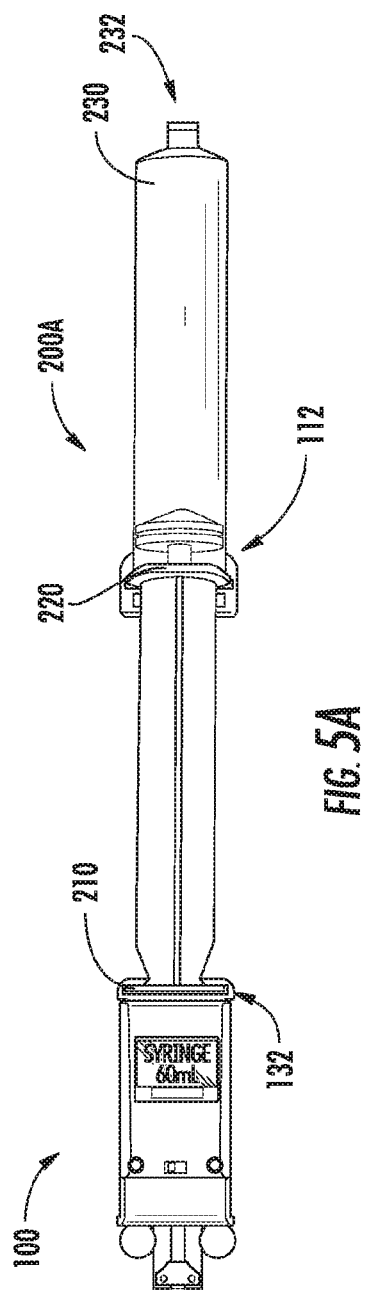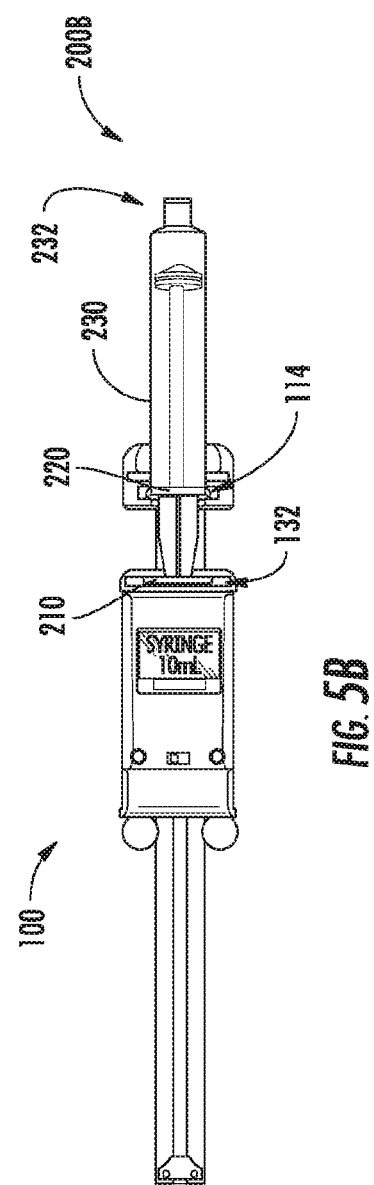

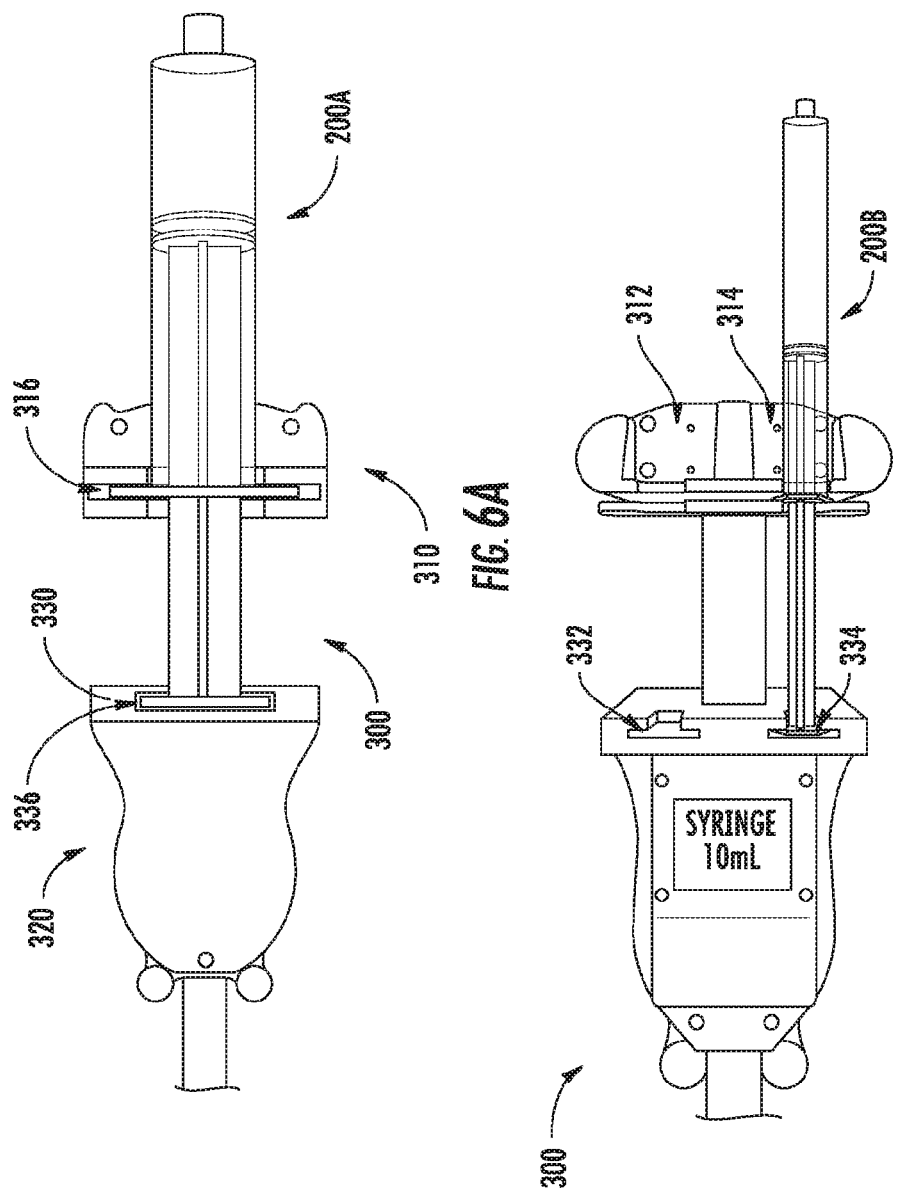

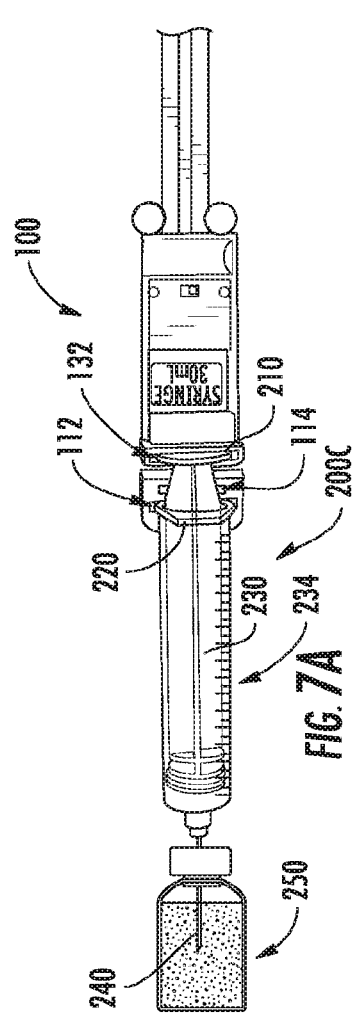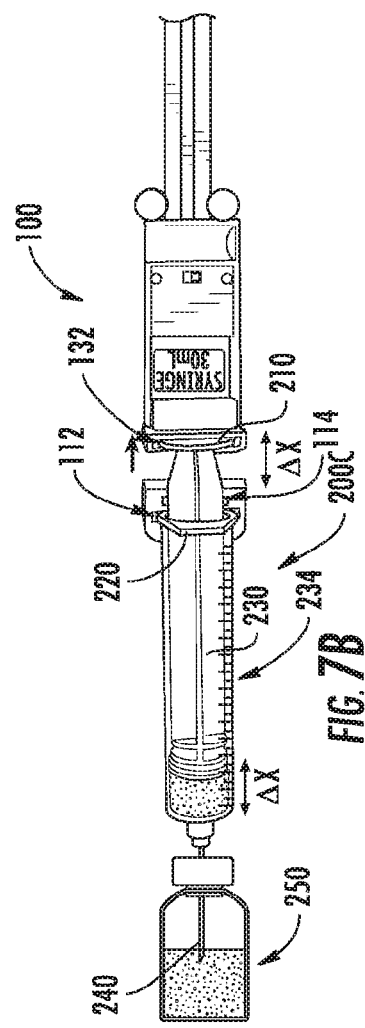

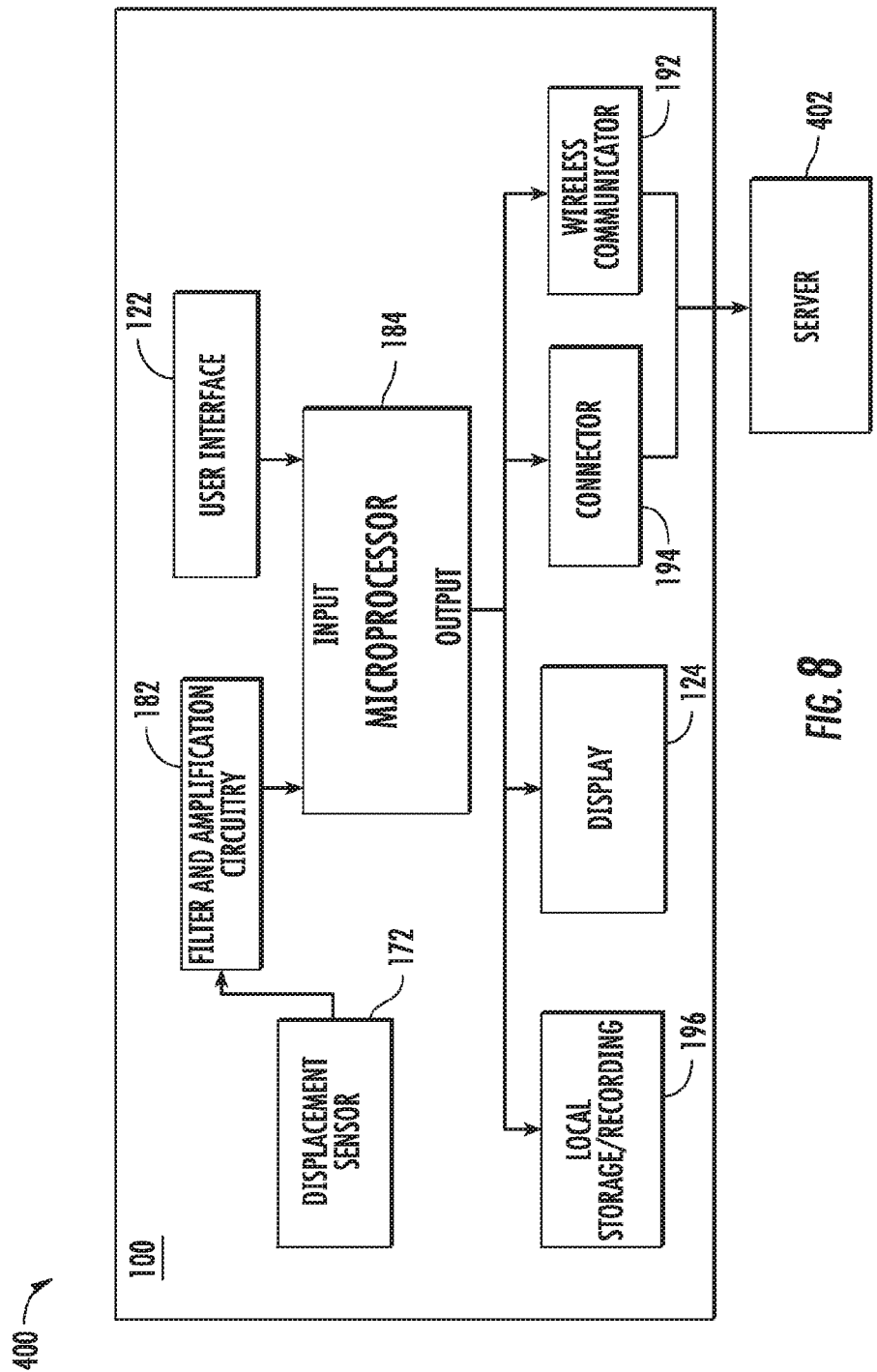

DEVICES, SYSTEMS, AND METHODS FOR VOLUMETRICALLY MEASURING SYRINGE FLUID

CROSS-REFERENCE TO RELATED APPLICATIONS

This application is a continuation of and claims priority to PCT/US2015/029488 which was filed on May 6, 2015 and which claims priority to U.S. Provisional Patent Application Ser. No. 61/988,972 filed May 6, 2014.

TECHNICAL FIELD

The presently disclosed subject matter generally relates to fluid measurement and transfer. More particularly, the presently disclosed subject matter relates to devices, systems, and methods for volumetrically measuring syringe fluids.

BACKGROUND

Cancer is the second most common cause of death in the United States. Treatments for this disease involve the administration of toxic chemicals to the body, which can be harmful in excessive doses and ineffective in inadequate doses. One method of cancer treatment is chemotherapy. Chemotherapy involves injectable drugs that target rapidly dividing cells for destruction. Rapidly dividing cells in the body are affected by the toxicity of the drug, and overexposure to the drug can lead to widespread tissue damage with a variety of symptoms. Thus, a goal of oncologists is to prescribe medications that are potent enough to significantly reduce the number of malignant cells without causing significant systemic damage to a patient.

In practice, chemotherapy doses are prepared by pharmacy technicians who transfer drugs from vials to patient-specific IV bags with syringes. The volumes that are required for each dose are calculated from the prescriptions and measured with a volumetric scale on a barrel of the syringe. However, preparing doses in this manner is notoriously imprecise and inaccurate. For example, one study concluded that only 86% of doses prepared in this manner are accurate to within 10% of the prescription, and only 72% of doses are accurate to within 5% of the prescription. The magnitude of this error is primarily a result of estimations made by the technicians who are using potentially inaccurate volumetric measurements on the syringes, themselves. Although, error may also be attributed to residual fluid left in the syringes after dispensing, and potentially other practices in the preparation of the dose. Thus, it is desirable to reduce error in the process of dose preparation by automating the dosage process, thereby removing the element of human estimation. While some automated dose-measuring systems exist, they are both expensive and too large for use in a fume hood or crowded laboratory setting.

Accordingly, a need exists for devices, systems, and methods for volumetrically measuring syringe fluids that provide users the ability to transfer prescribed drugs, in particular chemotherapy drugs, with greater precision and accuracy, without adding significant preparation time or cost, and while minimizing risk of contamination.

SUMMARY

Devices, systems, and methods for volumetrically measuring fluid are described herein. In one aspect, a device for volumetrically measuring fluid can comprise a reference plate, a flange adapter base attached at a first end of the reference plate for receiving a flange of a syringe, a plunger adapter disposed adjacent to a housing for receiving a plunger of the syringe, the plunger adapter being configured to slidingly move along a length of the reference plate, a displacement sensor disposed in the housing and configured to measure a displacement of the plunger adapter in relation to the flange adapter base as the plunger adapter is slid along the length of the reference plate, and a displacement conversion mechanism disposed in the housing and configured to convert the displacement measurement of the plunger adapter to a volumetric measurement in order to determine a volume of fluid the syringe has drawn in.

In another aspect, a system for volumetrically measuring fluid can comprise a device and a server or memory connected with the device. The device can comprise a reference plate, a flange adapter base attached at a first end of the reference plate for receiving a flange of a syringe, a plunger adapter disposed adjacent to a housing for receiving a plunger of the syringe, the plunger adapter being configured to slidingly move along a length of the reference plate, a displacement sensor disposed in the housing and configured to measure a displacement of the plunger adapter in relation to the flange adapter base as the plunger adapter is slid along the length of the reference plate, and a displacement conversion mechanism disposed in the housing and configured to convert the displacement measurement of the plunger adapter to a volumetric measurement in order to determine a volume of fluid the syringe has drawn in. The volume measurement is then recorded on the server or memory.

In still another aspect, a method for volumetrically measuring syringe fluid can comprise a barcode scanner to identify and/or record the type of liquid drawn with a device. The device can comprise a reference plate, a flange adapter base attached at a first end of the reference plate for receiving a flange of a syringe, a plunger adapter disposed adjacent to a housing for receiving a plunger of the syringe, the plunger adapter being configured to slidingly move along a length of the reference plate, a displacement sensor disposed in the housing, and a displacement conversion mechanism disposed in the housing. The method can further comprise securing the flange of the syringe to the flange adapter base and the plunger of the syringe to the plunger adapter, measuring, by the displacement sensor, a displacement of the plunger adapter in relation to the flange adapter base, as the plunger adapter is slidingly moved along the length of the reference plate, and converting, by the displacement conversion mechanism, the displacement measurement of the plunger adapter to a volumetric measurement in order to determine a volume of fluid the syringe has drawn in.

BRIEF DESCRIPTION OF THE DRAWINGS

The features and advantages of the present subject matter will be more readily understood from the following detailed description which should be read in conjunction with the accompanying drawings that are given merely by way of explanatory and non-limiting example, and in which:

FIG. 5A is an elevation view of an exemplary device for volumetrically measuring syringe fluid using, for example, a 60 mL syringe according to a first embodiment of the subject matter described herein;

FIG. 5B is an elevation view of an exemplary device for volumetrically measuring syringe fluid using, for example, a 10 mL syringe according to a first embodiment of the subject matter described herein;

FIG. 6A is an elevation view of an exemplary device for volumetrically measuring syringe fluid using, for example, a 60 mL syringe according to a second embodiment of the subject matter described herein;

FIG. 6B is an elevation view of an exemplary device for volumetrically measuring syringe fluid using, for example, a 10 mL syringe according to a second embodiment of the subject matter described herein;

FIG. 7A is an elevation view of an exemplary device for volumetrically measuring syringe fluid using, for example, a 30 mL syringe in an initial position according to a first embodiment of the subject matter described herein;

FIG. 7B is an elevation view of the exemplary device of FIG. 7B in a displacement position;

FIG. 8 is a schematic of an exemplary system for volumetrically measuring syringe fluid according to some embodiments of the subject matter described herein.

DETAILED DESCRIPTION

Figure 1:
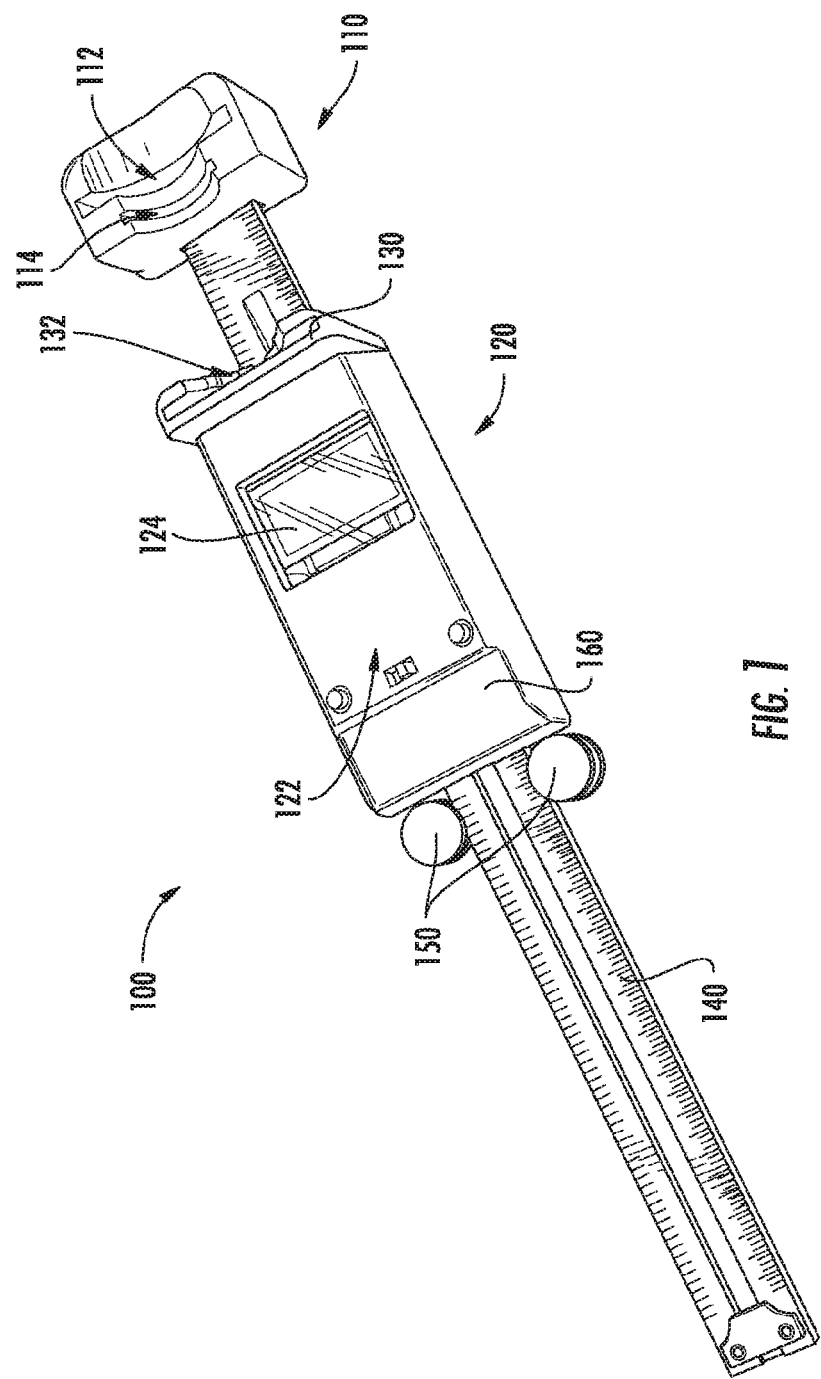
FIG. 1 is a perspective view of an exemplary device for volumetrically measuring syringe fluid according to a first embodiment of the subject matter described herein.

Devices, systems, and methods for volumetrically measuring syringe fluid are provided herein. In some aspects, the presently disclosed subject matter relates to the field of chemotherapy drug preparation for patient treatments. In other aspects, the presently disclosed subject matter relates to the field of general fluid measurement and transfer for clinical and research use, as well as for use in veterinary or other medicine. Accordingly, the present subject matter is in no way limited to use in preparation of chemotherapy drugs.

FIGS. 1-4 illustrate a first embodiment of device 100 for volumetrically measuring syringe fluids. Device generally designated 100 is configured to hold at least one syringe and to measure an amount of fluid drawn in by the at least one syringe with high accuracy and precision. In the field of chemotherapy, where there is a narrow therapeutic index between a toxic dose and a therapeutic dose, it is especially important to have improved accuracy and precision in determining an amount of chemotherapy drug that has been drawn into the syringe. Although it is known in the art to use automated dose-measuring systems for this exact reason, such systems can be expensive and too large for use in a fume hood or crowded laboratory setting. Thus, device 100 can advantageously provide a user (e.g., a pharmacy technician) with an ability to measure chemotherapy volumes from drug vials with greater precision and accuracy than current methods, without adding significant time to the technician's workload. Additionally, device 100 can minimize the risk of contact between the drug and the technician to prevent both contamination of the medicine and chemical harm to the technician, since device 100 is small enough to fit within a fume hood. Device 100 can also advantageously be durable enough to withstand multiple uses each day, but still be inexpensive to produce.

In some aspects, device 100 can comprise a flange adapter base generally designated 110 and a housing generally designated 120 in which a syringe generally designated 200 can be resiliently received and manipulated. Adapter base 110 and housing 120 can be composed of materials durable enough to withstand hundreds of uses (e.g., 200 uses) per day, while still being flexible enough to resiliently secure components of a syringe to device 100. For example, adapter base 110 and housing 120 can be composed of or comprise stainless steel, plastic, rubber, ceramic, or any other suitable material.

In some aspects, device 100 can be configured as a device that can comfortably fit in a user's hand. For example, device 100 can be approximately between one inch and two feet in length. Alternatively, device 100 can be configured for use primarily on a surface. For example, device 100 can be approximately two feet or larger in length.

In some aspects, adapter base 110 and/or housing 120 can comprise a plurality of slots for holding differently sized syringes. As is known in the art, syringes can come in different sizes according to various needs and a volume of medication needed to be dispensed by the syringe. Thus, device 100 can be provided with a plurality of slots that are configured to hold a plurality of differently sized syringes. In one such aspect, adapter base 110 can be configured to resiliently receive a flange of a syringe (e.g., 220, FIGS. 5A-5B) to device 100. As illustrated in FIG. 1, a first adapter slot generally designated 112 and a second adapter slot generally designated 114 can be disposed on a top surface of adapter base 110. However, in other aspects, slots 112, 114 can be disposed on a different surface or each slot on different surfaces of base 110. Slot 112 and slot 114 can also comprise two differently sized slots each being configured to resiliently hold varying sizes of syringe flanges, which increase and/or decrease in size depending on a size of the syringe. For example, first adapter slot 112 can be configured to resiliently accommodate 20 mL, 30 mL, and 60 mL syringes, while second adapter slot 114 can be configured to resiliently accommodate 1 mL, 2 mL, 3 mL, 5 mL, and 10 mL syringes. In some aspects, a slot can be configured to accommodate 1 mL, 2 mL, 3 mL, 5 mL, 10 mL, 20 mL, 30 mL, and 60 mL syringes (see, e.g., 316, FIGS. 6A-6B).

Housing 120 can be configured to resiliently receive a plunger of a syringe (e.g., 210, FIGS. 5A-5B) to device 100. As illustrated in FIG. 1, housing 120 can comprise a plunger head adapter 130 at one end. Plunger head adapter 130 can be separate from or integral with housing 120 and can be composed of or comprise a same or a different material. Plunger head adapter 130 can comprise a slot or a plurality of slots for resiliently securing a plunger of the syringe. For example, plunger head adapter 130 can comprise one resilient slot 132 for accommodating variously sized plungers of differently sized syringes (e.g., 1 mL, 2 mL, 3 mL, 5 mL, 10 mL, 20 mL, 30 mL, and 60 mL syringe). Resilient slot generally designated 132 can be disposed on a top surface of plunger head adapter 130, such that slot 132 is in a plane substantially parallel to slots 112 and 114. Accordingly, a plunger of a syringe can be resiliently received by slot 132 and a flange of a syringe can be resiliently received by one of slots 112 or 114 depending on a size of the syringe.

Figure 2:
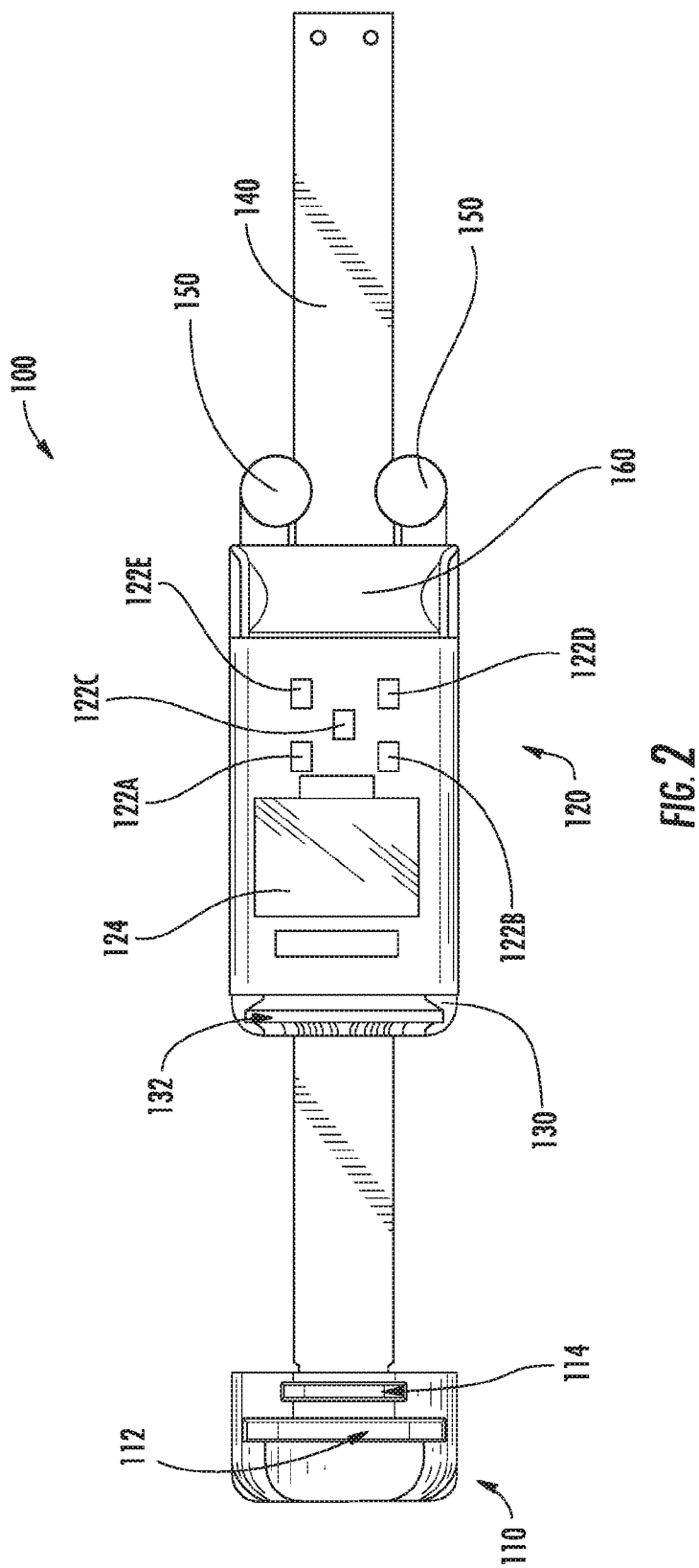
FIG. 2 is an elevation view of an exemplary device for volumetrically measuring syringe fluid according to a first embodiment of the subject matter described herein.
Figure 3:
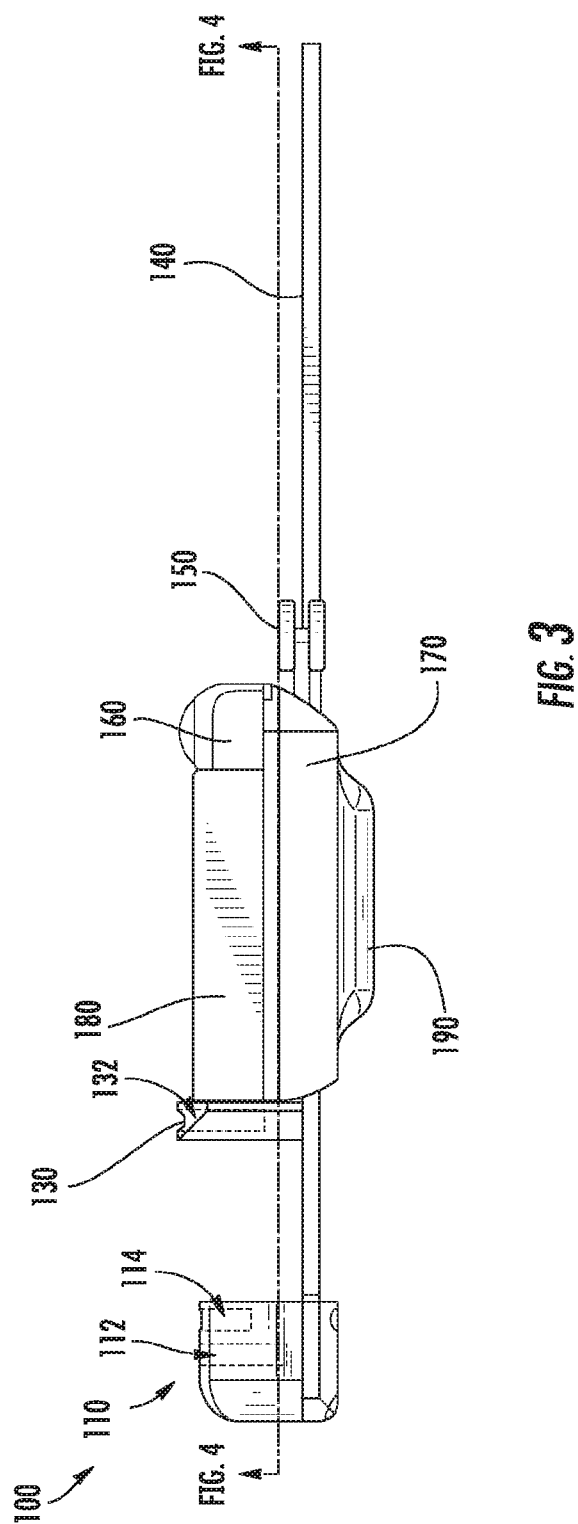
FIG. 3 is a side view of an exemplary device for volumetrically measuring syringe fluid according to a first embodiment of the subject matter described herein.
Figure 4:
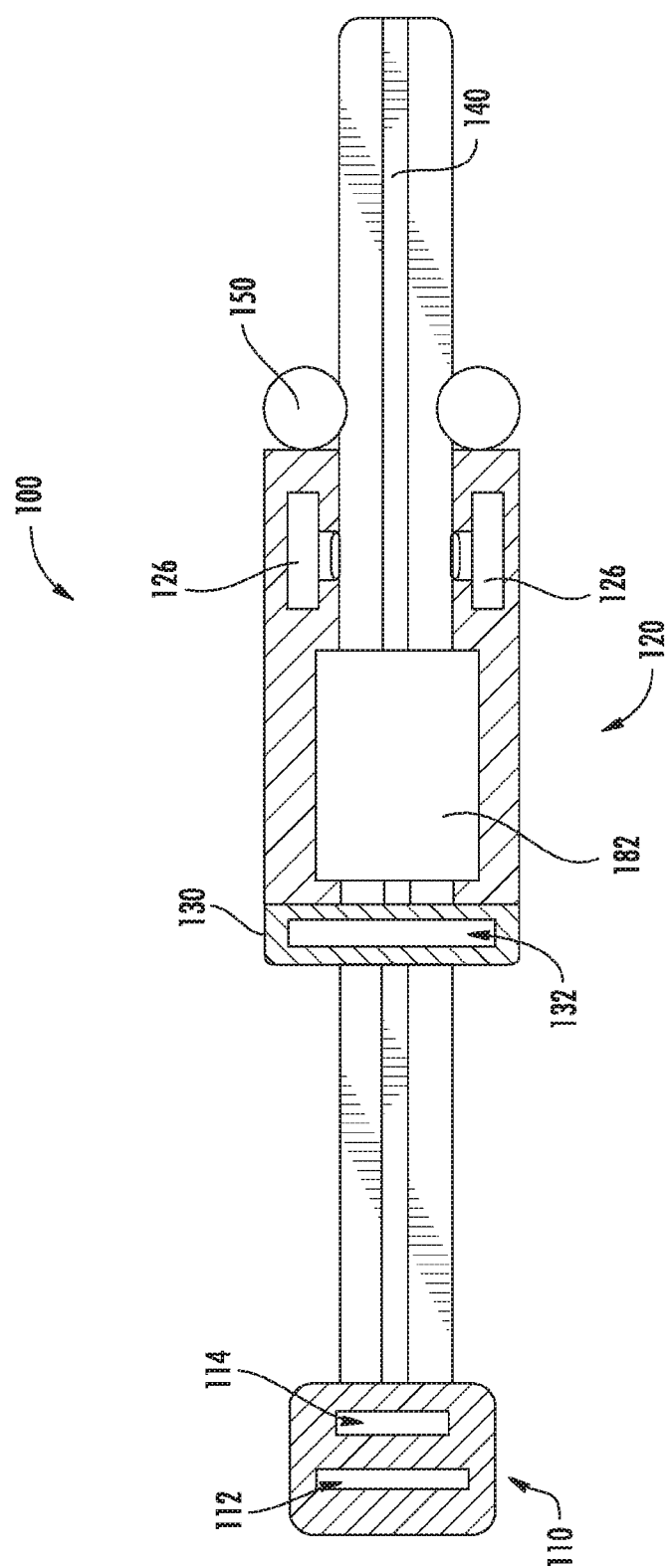
FIG. 4 is a cross-sectional view of the exemplary device of FIG. 3.

Housing 120 can further comprise a user interface generally designated 122 for user interaction with device 100. User interface 122 can comprise a plurality of buttons and/or switches 122A-E (shown in FIG. 2) corresponding to particular device functionality and a display 124. In some aspects, as illustrated in FIG. 2, the plurality of buttons and/or switches 122A-E can comprise, for example, a syringe size selection button 122A, button 122B for zeroing device 100, a measurement repetition mode button 122C, a button 122D for mechanically locking motion of device 100 and saving a measurement, and a button 122E for transmitting a saved measurement to a server. Plurality of buttons and/or switches 122A-E can also comprise a switch for connecting a power supply to a rest of a circuit of device 100. Additionally, device 100 may be provisioned with a button and/or switch for translating a sensor signal to displacement data, converting displacement data to volume data, transferring data to a wireless transmitter, displaying certain data on display 124 (e.g., volume of the measurement, syringe size, battery life, indicator for measurement repeating mode, indicator for remote server connection, etc.).

Display 124 can be a digital display that is configured to display, for example and without limitation, syringe size, volume of fluid that has been collected or expelled, a saved measurement if device 100 has been locked, an indicator for measurement repeating mode, a state of a wireless connection, and/or remaining battery life. Other information can also be displayed on display 124 relevant to use of device 100. In some aspects, display 124 can be disposed adjacent to plurality of buttons and/or switches 122A-E for quick visual reference of any selections made by user interaction with buttons 122A-E.

Base 110 and plunger adapter 130 can be displaceable in regard to one another via a reference sensor plate 140. Reference sensor plate 140 can be configured to be fixedly attached to base 110. For example, as illustrated in FIG. 1, base 110 is fixedly attached to one end of reference sensor plate 140. Reference sensor plate 140 can be configured to be movably to plunger adapter 130 via housing 120. For example, as illustrated in FIG. 1, housing 120 is slidingly moved at a bottom surface to reference sensor plate 140 and can be slid along an axial length of reference sensor plate 140 until locked into place via clamping mechanism 126 (see, FIG. 4). Clamping mechanism 126 can comprise an electromagnetic clamp or other electrically-engaged mechanism for preventing motion of plunger adapter 130 on reference sensor plate 140 with respect to base 110, and can be actuated by device 100. For example, clamping mechanism 126 can be actuated by a user interfacing with button 122D for mechanically locking displacement of plunger adapter 130 via preventing housing 120 from sliding on reference plate 140, and also saving a displacement measurement. In this example, after clamping mechanism 126 is actuated, mechanism 126 can be configured to lock housing 120 at its current position along axial length of reference sensor plate 140 and then temporarily store (e.g., in local storage, 186, FIG. 8) a displacement measurement Δx (see, FIGS. 7A-7B) as measured between base 110 and plunger adapter 130.

In some aspects, clamping mechanism 126 can be utilized by specific functionality of device 100. The clamping mechanism can be a friction type connection, a screw fastener, a tab fastener or any other clamping type fastener. For example, a repeating mode of device 100 can be activated to repeat volume measurements by a user interfacing with button 122C, which can disengage clamping mechanism 126 and can reset temporarily stored measurements to zero. In this example, clamping mechanism 126 can automatically reengage when a subsequent volumetric measurement is again equal to the temporarily stored value.

In this manner, reference sensor plate 140 can be composed of or comprise a material that enables substantially frictionless movement along its length. For example, reference sensor plate 140 can be composed of or comprise stainless steel, plastic, rubber, ceramic, or any other suitable material. In some aspects, oil, grease, and/or any other lubricant can be used so that housing 120 can slide smoothly on plate 140. Reference sensor plate 140 can comprise a plurality of demarcations or indicators (not shown) along its axial length to visually denote displacement of plunger adapter 130 from base 110. In some aspects, the demarcations or indicators denote a displacement measurement in millimeters (mm), inches (in), and/or any other measurement standard.

In some aspects, axial movement of housing 120 along reference sensor plate 140 can be accomplished through two types of adjustments: coarse adjustment and fine adjustment. Coarse adjustment of housing 120 along reference sensor plate 140 can be accomplished through a user manually grasping housing 120 and moving it along the axial length of sensor plate 140. However, for finer adjustments of housing 120 in relation to sensor plate 140, fine adjustments using a fine adjustment mechanism 150 can be utilized. Fine adjustment mechanism 150 can be rotatably attached to housing 120 (e.g., disposed within displacement sensor housing 170) at an end opposing the end at which plunger head adapter 130 is positioned. Fine adjustment mechanism 150 can comprise, for example, two friction-based cylindrical wheels, one being disposed on either side of reference sensor plate 140. The wheels of fine adjustment mechanism 150 can comprise for example stainless steel, plastic, rubber, ceramic, or any other suitable material. Housing 120 can be configured to fixedly hold fine adjustment mechanism 150 against the sides of sensor plate 140, such that pressing and rotating either a left or right wheel of fine adjustment mechanism 150 can use friction to incrementally slide housing 120 an axial distance along plate 140. In some aspects, fine adjustment mechanism 150 can slide housing 120 along plate 140 by smaller increments than by coarse adjustment. Accordingly, larger adjustments of housing 120 can be made through coarse adjustment of housing 120 in relation to sensor plate 140, whereas fine adjustment mechanism 150 can be utilized for making smaller adjustments at smaller increments.

Notably, displacement of housing 120 along sensor plate 140 results in a plunger of a syringe resiliently received in plunger adapter 130 also being displaced in relation to a flange of the syringe received in base 110, which will be discussed in more detail below. Thus, more or less medicine may be aspirated from a vial of medicine based on a distance that plunger adapter 130 is displaced from base 110.

Housing 120 can further comprise, for example, a distance measurement system, a displacement-to-volume conversion system, and/or a data transmission system. In particular, electronics and circuitry, as well as a circuitry power supply, needed for each of these individual systems can be stored in housing 120. The embodiment of device 100 illustrated in FIGS. 1-4 provide for a battery (not shown) to provide power to device 100. However, other types of providing power (e.g., replaceable battery(s), rechargeable battery(s), wall adapter, etc.) to device 100 are also contemplated. Where device 100 is powered by a battery, battery can be disposed in housing 160 accessible from a top surface of housing 120. A power switch can be disposed in user interface 122 so that power to device 100 can be controlled by a user.

A distance measurement system can be used by device 100 in order to measure displacement of a syringe plunger within a syringe barrel from a syringe flange. In this regard, the distance measurement system can use reference plate 140 as a reference for measuring the distance between the syringe plunger and the syringe flange. For example, a distance between a first position of plunger adapter 130 and a second position of plunger adapter 130 on sensor plate 140 can be a displacement distance Δx. Where a syringe (e.g., 200) is secured to device 100 in a manner described above, displacement of adapter 130 from base 110 corresponds to a displacement distance Δx of a syringe plunger within a barrel of the syringe. As such, the displacement-to-volume system can convert a displacement of the syringe plunger within the barrel of the syringe to a volume of material (e.g., air, fluid, etc.) that has been drawn in or expelled from the syringe. This converted value can be displayed on a user interface associated with device 100 and/or transmitted to a remotely located computing platform for electronic storage, verification of dosage, etc.

In some aspects, the distance measurement system can use at least one distance or displacement mechanism housed in displacement sensor housing 170 for determining a displacement of adapter 130 from base 110. For example, the at least one distance reference mechanism can comprise: at least one capacitive sensor, at least one laser sensor, at least one drop line sensor, at least one inductive sensor, at least one rod capacitive sensor, at least one sonic sensor, at least one linear variable differential transformer (LVDT) whose distance measurement points are attached to the plunger head adapter 130 and the flange adapter base 110, or any combination thereof. Additional distance reference mechanisms can also be utilized. In the embodiment of device 100 illustrated in these figures, however, a capacitive sensor 172 (see, FIG. 8) is used. Capacitive sensor 172 can be fixedly attached to plunger head attachment 130 of device 100. Sensor 172 can be configured to measure the distance between an initial position and a second, displacement position of a plunger of a syringe in reference to a flange of the syringe as housing 120 is slid along plate 140. For example, as housing 120, to which plunger head adapter 130 is attached, is slid along reference plate 140, sensor 172 can measure in real-time a distance between plunger head adapter 130 and flange adapter base 110.

In some aspects, capacitive sensor 172 can transmit this measurement in the form of a signal, pulse, or other electronic communication to circuitry 182 for application of a filter(s), adjustment, amplification, and/or other signal processing. Circuitry 182 can be a component of the displacement-to-volume conversion system, which can be housed within an electronics housing 180. Circuitry 182 of the volume-to-displacement conversion system can comprise capacitive plates, a signal generator, a signal interpreter, a microprocessor (e.g., 184, FIG. 8), an amplification stage for sensor output signal, a stage which delivers the amplified sensor signal to a microprocessor, a display (e.g., 124 stored on housing 120 as a component of user interface 122), a stage which relays real-time volume measurement from the microprocessor to the display, a stage that relays user input to the microprocessor, and a stage for wireless transmission of measurement data to a server (e.g., 402, FIG. 8) for converting the displacement measurement into a volume measurement. Other components of circuitry 182 can also be utilized.

In some aspects, the displacement measurement signal can be transmitted to a microprocessor of the volume-to-displacement conversion system for scalar conversion to a volume measurement. For example, the microprocessor can be configured as a microprocessor 184 comprising a programmable integrated circuit configured to convert the displacement measurement to a volumetric measurement based on a syringe size. In particular, a calibration function or coefficient corresponding to each syringe size (e.g., 1 mL, 2 mL, 3 mL, 5 mL, 10 mL, 20 mL, 30 mL, and 60 mL) can be stored in a local database (e.g., data storage 196) for computation by microprocessor 184 with the displacement measurement signal. In some aspects, device 100 can be provisioned with a user interface for selecting syringe size. For example, a user can select a syringe size using syringe size selection button 122A at user interface 122. Microprocessor 184 can thereby be provided with data regarding each syringe size, so that upon selection of syringe size, microprocessor 184 need only locate and access such data from a local database (e.g., data storage 196). Once the appropriate syringe size has been selected, microprocessor 184 can be configured to apply the distance measurement and input the measurement into the appropriate conversion mathematics in order to output a volumetric measurement of fluid drawn in by the syringe. In some aspects, the volumetric measurement can be displayed on user interface 122 (e.g., display 124) in real-time. In other aspects, for example, the volumetric measurement can be transmitted to a remote computing platform for remote storage, verification, etc.

In some aspects, the programmable integrated circuit of microprocessor 184 can be configured to perform specific device functions associated with converting a displacement measurement into a volumetric measurement. To achieve this functionality, the programmable integrated circuit can comprise an algorithm to provide device 100 with functionality for reading a sensor signal, converting the sensor signal to displacement data, converting displacement data to a volume measurement, resetting volume measurements to zero, sending converted volume measurements to digital display (e.g., display 124), recording locked data, sending a signal to locking mechanism (e.g., clamping mechanism 126), and including a measurement repeating mode. Other functionality not listed is also contemplated to be included. An exemplary algorithm for performing such functionality associated with device 100 is set forth below:

```
#include <16F1829.h>
#device icd=true #use delay (clock = 16000000)
#include <oled__16F1829__i2c.h>
#include <MATH.H>
#include <interrupt_control.h>
#fuses INTRC_IO, NOWDT, PUT
#define DATA PIN__C3 unsigned int idx = 0;
unsigned int rupt = 0; float num_out = 0;
float pwr_exp = 0; float num_total = 0;
float measurment_MM = 0;
unsigned long int Num = 0; unsigned int num_in = 0;
unsigned int min_in = 0;
unsigned int mode = 0;
unsigned int syringe = 0;
#int_EXT
void EXT_isr(void) {
    num_in = input(PIN_C3);
    rupt = 1;
    Num = 0;
}
void main ( ){
// display on OLED
    SETUP_OSCILLATOR(OSC_16MHZ|OSC_INTRC);
        delay_us(10);
output_low(ress);
    delay_us(20);
    output_high(ress);
```

```
        delay_us(20);
    initialise_screen( );
        delay_us(10);
        clear_screen( );
        delay_us(10);
        fill_screen( );
        delay_us(10);
        clear_screen( );
        delay_us(10);
    oled_write_command(0xb0);
    oled_write_command(0x00);
    oled_write_command(0x10);
    oled_zoom( );
        disable_interrupts(GLOBAL);
        setup_timer_1(T1_INTERNAL|T1_DIV_BY_1);
    setup_comparator(NC_NC_NC_NC);
        enable_interrupts(INT_EXT);
        ext_int_edge(0,L_TO_H);
        enable_interrupts(GLOBAL);
        while (true){
            Num = Num +1;
            if (Num >= 15000){
                idx = 0;
                Num = 0;
            } //if
            if (input(PIN_C4)){
                delay_ms(10);
                if (input(PIN_C4)==1){
                    while (input(PIN_C4)){
                        delay_ms(1);
                    }
                    mode=mode +1;
                }
            }
            if (rupt == 1){
                if (idx == 0){
                    num_out = num_in;
                    num_total = num_total + num_out;
                }
                if (idx == 1){
                    num_out = num_in * 2;
                    num_total = num_total + num_out;
                }
                if (idx == 2){
                    num_out = num_in * 4;
                    num_total = num_total + num_out;
                }
                if (idx == 3){
                    num_out = num_in * 8;
                    num_total = num_total + num_out;
                }
                if (idx == 4){
                    num_out = num_in * 16;
                    num_total = num_total + num_out;
                }
                if (idx == 5){
                    num_out = num_in * 32;
                    num_total = num_total + num_out;
                }
                if (idx == 6){
                    num_out = num_in * 64;
                    num_total = num_total + num_out;
                }
                if (idx == 7){
                    num_out = num_in * 128;
                    num_total = num_total + num_out;
                }
                if (idx == 8){
                    num_out = num_in * 256;
                    num_total = num_total + num_out;
                }
                if (idx == 9){
                    num_out = num_in * 512;
                    num_total = num_total + num_out;
                }
                if (idx == 10){
                    num_out = num_in * 1024;
                    num_total = num_total + num_out;
                }
                if (idx == 11){
                    num_out = num_in * 2048;
                    num_total = num_total + num_out;
                }
                if (idx == 12){
                    num_out = num_in * 4096;
                    num_total = num_total + num_out;
                }
                if (idx == 13){
                    num_out = num_in * 8192;
                    num_total = num_total + num_out;
                }
                if (idx == 14){
                    num_out = num_in * 16384;
                    num_total = num_total + num_out;
                }
                if (idx == 15){
                    num_out = num_in * 32768;
                    num_total = num_total + num_out;
                }
                if (idx == 16){
                    num_out = num_in * 65536;
                    num_total = num_total + num_out;
                }
                if (idx >= 23){
                    if (num_in == 1){
                        num_total = num_total * −1;
                    }
                    //Store measurement, print to screen and RESET idx
                    //   measurement_MM = num_total / 100;
                    if (mode == 0) {   // 1ml y = 0.0172x − 0.0113
                        //   measurment_MM = ((0.0172 * num_total)) / 100 ;
                        syringe = 1;
                    }
                    if (mode == 1) {   // 3ml y = 0.0565x − 0.001
                        //   measurment_MM = ((0.0565 * num_total)) / 100 ;
                        syringe = 3;
                    }
                    if (mode == 2) {   // 5ml y = 0.1103x + 0.0033
                        //   measurment_MM = ((0.1103 * num_total)) / 100 ;
                        syringe = 5;
                    }
                    if (mode == 3) {   // 10ml y = 0.1618x − 0.0189
                        //   measurment_MM = ((0.1618 * num_total)) / 100 ;
                        syringe = 10;
                    }
                    if (mode == 4) {   // 20ml y = 0.2794x + 0.0015
                        //   measurment_MM = ((0.2794 * num_total)) / 100 ;
                        syringe = 20;
                    }
                    if (mode == 5) {   // 30ml y = 0.3606x − 0.008
                        //   measurment_MM = ((0.3606 * num_total)) / 100 ;
                        syringe = 30;
                    }
                    if (mode == 6) {   // 60ml y = 0.5472x − 0.003
                        //   measurment_MM = ((0.5472 * num_total)) / 100 ;
                        syringe = 60;
                    }
                    if (mode >= 7) {   // Clear
                        mode = 0;
                    }
                    num_total = 0;
                    num_out = 0;
```

```
            oled_gotoxy(0,0);
            printf(oled_printchar,"Syring
            e %2.0u", syringe );
            printf(oled_printchar,"mL");
            oled_gotoxy(2,0);
            printf(oled_printchar," mL =
            %2.3g", measurment_MM );
            idx = 0;
        }
        rupt = 0;
        idx = idx+1;
    }
    } //while
}//main
```

Hardware and/or software for relaying data to an external server can be stored in a housing 190. For example, a wireless transmitter 192 (see, FIG. 8) can be stored in a wireless transmitter housing 190. Transmitter 192 can be functionally connected with a wireless connector 194 (see, FIG. 8) that can relay data (e.g., volumetric measurements) to an electronic interface of a server 402 that is configured to store electronic medical records and/or verify dosage amounts. A local repository, storage or database 196 (see, FIG. 8) associated with device 100 can temporarily store data until data is transmitted to the electronic interface. Exemplary data storage may include non-transitory computer readable media, such as flash memory, random access memory, or other storage devices. For example, where there is no wireless connection, battery is low, etc., device 100 can temporarily store volumetric measurement records in local database 196. In some aspects, data storage may be external.

In some aspects, a scanner (not shown) for reading dosages that are to be dispensed can also be included in device 100. The scanner may comprise a bar code scanner, a QR code scanner, or any other scanner known in the art. Upon scanning a bar code using the scanner, information regarding a particular dosage can be displayed at display 124 of device 100. Additionally, the scanner can be configured to provide a warning on display 124 if an amount displayed and an amount of medicine withdrawn by device 100 are not within a specified, acceptable threshold of one another. Circuitry and other electronics and/or components associated with the scanner can be housed in housing 120 of device 100.

Now referring to FIGS. 5A-5B, a first embodiment of device 100 is illustrated with a syringe, generally designated 200, with two different size syringes secured into adaptor base 110 and plunger adapter 130. In FIG. 5A, a 60 mL syringe 200A is secured to device 100. In particular, a plunger 210 of syringe 200A is resiliently secured to slot 132 while a flange 220 of syringe 200A is secured in slot 112 of base 110. Since syringe 200A is a 60 mL syringe, flange 220 is secured to the larger of the two resilient slots, which is slot 112. By comparison, in FIG. 5B a 10 mL syringe 200B is secured to device 100. Notably, while plunger 210 is still resiliently secured to slot 132, flange 220 is resiliently secured in slot 114 of base 110. This is because slot 114 is configured to resiliently receive syringes of smaller sizes than slot 112. Accordingly, regardless of the size of syringe 200, as plunger adapter 130 is slid along reference plate 140 via housing 120, plunger 210 can be configured to slide in and out of barrel 230 of the syringe.

FIGS. 6A-6B illustrate a second embodiment of the device, generally designated 300. Device 300 can provide the same functionality and materials as device 100, but can comprise three separate slots for receiving differently sized flanges of a syringe, as well as three separate slots for receiving accompanying sized syringe plungers. Notably, device 300 can hold up to three differently or similarly sized syringes at one time for volumetric measurement thereof. As a result, it will be understood by one of skill in the art that the subject matter disclosed herein can be configured in any manner in which multiple sized syringes can be securely received either at one time or individually.

In particular, device 300 can comprise a flange adapter base generally designated 310 configured to resiliently secure a flange of a syringe (e.g., 220) to device 300. As illustrated in FIGS. 6A-6B, a first adapter slot generally designated 312 and a second adapter slot generally designated 314 can be disposed on a top surface of adapter base 310, while a third adapter slot 316 can be disposed on an opposing bottom surface of adapter base 310. Slots 312 and 314 can be disposed adjacent to one another such that two syringes may be securely received in each of the slots at a same time. Since third adapter slot 316 is disposed at an opposing surface of base 310, a third syringe may be simultaneously securely received in third adapter slot 316. First adapter slot 312, second adapter slot 314, and third adapter slot 316 can comprise a same or differently sized slots each being configured to resiliently receive varying sizes of syringe flanges, which increase and/or decrease in size depending on a size of the syringe. For example, first adapter slot 312 can be configured to resiliently accommodate 20 mL, 30 mL, and 60 mL syringes, while second adapter slot 314 can be configured to resiliently accommodate 1 mL, 2 mL, 3 mL, 5 mL, and 10 mL syringes. In some aspects, each of slots 312 and 314 can accommodate syringes of a same size. Third adapter slot 316 can be configured to accommodate 1 mL, 2 mL, 3 mL, 5 mL, 10 mL, 20 mL, 30 mL, and 60 mL syringes.

Device 300 can also comprise a housing 320 configured to resiliently receive a plunger of a syringe. Housing 320 can comprise a plunger head adapter 330 at one end. Plunger head adapter 330 can be separate from or integral with housing 320 and can be composed of or comprise a same or a different material. Plunger head adapter 330 can comprise a slot or a plurality of slots for resiliently securing a plunger of the syringe. For example, plunger head adapter 330 can comprise three resilient slots, a first resilient slot generally designated 332, a second resilient slot generally designated 334, and a third resilient slot 336 for accommodating variously sized plungers of differently sized syringes (e.g., 1 mL, 2 mL, 3 mL, 5 mL, 10 mL, 20 mL, 30 mL, and 60 mL syringe). For example, first slot 332 can be configured to resiliently accommodate 20 mL, 30 mL, and 60 mL syringe plungers, while second slot 334 can be configured to resiliently accommodate 1 mL, 2 mL, 3 mL, 5 mL, and 10 mL syringe plungers. In some aspects, each of slots 332 and 334 can accommodate syringe plungers of a same size. Third adapter slot 336 can be configured to accommodate 1 mL, 2 mL, 3 mL, 5 mL, 10 mL, 20 mL, 30 mL, and 60 mL syringe plungers. In some aspects, for example, resilient slots 332 and 334 can be disposed on a top surface of plunger head adapter 330, such that slots 332 and 334 are in a plane substantially parallel to slots 312 and 314. In this aspect, third resilient slot 336 can be disposed on an opposing bottom surface of plunger head adapter 330, such that third resilient slot 336 is in a plane substantially parallel to third slot 316 disposed on the opposing bottom surface of base 310. Accordingly, a plunger of a syringe can be resiliently received by any one of first resilient slot 332, second resilient slot 334, or third resilient slot 336, and a flange of a syringe can be resiliently received by a corresponding one of first slot 312, second slot 314, or third slot 336, depending on a size of the syringe.

As illustrated in FIG. 6A, a 60 mL syringe 200A is illustrated as being securely received in device 300. In particular, a plunger of syringe 200A is received in a third resilient slot 336 disposed on a plunger adapter 330, while a flange of syringe 200A is received in a third resilient slot 316 disposed on a flange adapter base 310. By comparison, as illustrated in FIG. 6B, a 10 mL syringe 200B is illustrated as being securely received in device 300. In particular, a plunger of syringe 200B is received in slot 334 while a flange of syringe 200B is received in slot 314.

Now referring to FIGS. 7A-7B, a first embodiment of device 100 is illustrated securely receiving a 30 mL syringe 200C aspirating a fluid from a vial 250. However, as described above, a syringe between the sizes of 1 mL and 60 mL may be securely held by device 100. In FIG. 7A, syringe 200C is illustrated prior to aspirating any fluid from vial 250, while in FIG. 7B syringe 200C is illustrated in the process of aspirating fluid from vial 250.

Specifically, in FIG. 7A, device 100 securely holds syringe 200C at an initial position, where a plunger 210 and a flange 220 of syringe 200C are disposed proximate to one another. Plunger 210 of syringe 200C may be resiliently secured in slot 132 of plunger head adapter 130, while flange 220 of syringe 200C may be resiliently secured in slot 112 of base 110. When syringe 200C is secured in an initial position, no liquid or fluid can be aspirated into a barrel 230 of the syringe. Opposing flange 220 is an open end 232 of barrel 230. At open end 232, a hypodermic needle 240 may be attached using any suitable method. Needle 240 may be inserted into vial 250 for aspirating medicine therefrom.

In FIG. 7B, device 100 has been manipulated by a user using either coarse adjustments or fine adjustment knobs 150 to displace or slidingly adjust housing 120 from a first position to a second position with regard to reference plate 140. Thus, housing 120 is displaced an amount equivalent to Δx. Since plunger 210 is secured to adapter 130 and flange 220 is secured to base 110, plunger 210 can also be displaced from base 110 an amount equivalent to Δx. In other words, as housing 120 is moved along reference plate 140, plunger 210 of syringe 200C is simultaneously moved a corresponding amount. By grasping and moving housing 120 along with plunger 210, a corresponding volume of fluid may be aspirated into barrel 230 of syringe 200C until a desired dosage amount is acquired. Although not illustrated in FIG. 7B, a reference mechanism (e.g., capacitive sensor 172) can be utilized by device 100 for determining a displacement of syringe plunger 210 in relation to a barrel 230 of syringe 200C. The reference mechanism can be configured to transmit this measurement in the form of a signal, pulse, or other electronic communication to circuitry 182 for application of a filter(s), adjustment, amplification, and/or other signal processing. The processed displacement measurement can be converted to a volumetric measurement using a stored calibration function or coefficient corresponding to the syringe size. The volumetric measurement can then be displayed on user interface (e.g., display 124). In one exemplary embodiment, device 100 is configured to draw more fluid than desired into barrel 230 of syringe 200C, such that fine adjustments using fine adjustment knobs 150 can be made until the exact dosage amount is attained.

Accordingly, device 100 can be used to measure a displacement of plunger of syringe 200 and convert said displacement measurement to a volume measurement as a way to more precisely and accurately measure fluid intake of a syringe. Device 100 can be accurate between approximately at least ±5% to ±0.01% by weight. Preferably, device 100 is accurate to at least approximately ±0.3% by weight. This is in stark contrast to conventional practices where only 86% of doses are accurate to within 10% of a dosage amount and only 72% are accurate to within 5% of the dosage amount. Such a device 100 is advantageous in the dose preparation process of chemotherapy drugs due to the narrow therapeutic range such drugs have.

Referring to FIG. 8, a system generally designated 400 for increased precision and accuracy of fluid transfer from a syringe can in some aspects comprise a device 100 and a server 402 communicatively connected to device 100. In some aspects, device 100 can be a device of either the first or second embodiment described above, although other configurations of device 100 are also contemplated.

Device 100 may be configured to securely hold a syringe, which may be provided by a user of the device. For example, a user may interface with device 100 by securing a flange of a syringe (e.g., syringe 200) to a flange adapter base 110 and a plunger of the syringe to a plunger adapter 130 of the device. In addition, device 100 may be configured to be manipulated by the user in order to draw in or expel fluids from a syringe secured to the device. For example, the user may grasp and move a housing 120 including plunger adapter 130 along a reference plate 140 in order to draw in or expel a quantity of liquid into or from a barrel of the syringe.

In some aspects, device 100 can comprise a user interface allowing a user to interface with device 100. For example, a user can press one of a plurality of buttons and/or switches that can be disposed on user interface 122, such as, a syringe size selection button 122A, button 122B for zeroing device 100, a measurement repetition mode button 122C, a button 122D for mechanically locking the motion and saving a measurement, and/or a button 122E for transmitting a saved measurement to a server. Selections made by the user at user interface 122 may be transmitted as input to a microprocessor 184.

Device 100 may also comprise a displacement reference mechanism for measuring a displacement between a flange of a syringe in reference to a plunger of the syringe in order to determine a volumetric measurement of fluid drawn into a barrel of the syringe. For example, the displacement reference mechanism can comprise at least one displacement sensor 172. In some aspects, at least one displacement sensor 172 can be at least one capacitive sensor, at least one laser sensor, at least one drop line sensor, at least one inductive sensor, at least one rod capacitive sensor, at least one sonic sensor, at least one linear variable differential transformer (LVDT) whose distance measurement points are attached to plunger head adapter 130 and flange adapter base 110, or any combination thereof. In this example, displacement sensor 172 can be configured to measure a displacement Δx between an initial position and a second, displacement position of a flange of a syringe in reference to a plunger of the syringe as housing 120 is slid along plate 140.

In some aspects, capacitive sensor 172 can transmit this measurement in the form of a signal, pulse, or other electronic communication to circuitry 182 for application of a filter(s), adjustment, amplification, and/or other signal processing. Circuitry 182 can be a component of the displacement-to-volume conversion system, which can be housed within an electronics housing 180 of device 100.

In some aspects, circuitry 182 can transmit the processed signal to microprocessor 184 for conversion to a volumetric measurement. Microprocessor 184 can comprise a programmable integrated circuit configured to convert the displacement measurement to a volumetric measurement based on a syringe size. In particular, a calibration function or coefficient corresponding to each syringe size (e.g., 1 mL, 2 mL, 3 mL, 5 mL, 10 mL, 20 mL, 30 mL, and 60 mL) can be stored in a local database (e.g., data storage 196) for computation by microprocessor 184 with the displacement measurement signal. For example, a user can select a syringe size using syringe size selection button 122A at user interface 122. Microprocessor 184 can be provided with data regarding each syringe size, so that upon selection of syringe size, microprocessor 184 need only locate and access such data from a local database (e.g., data storage 196). Once the appropriate syringe size has been selected, microprocessor 184 can be configured to apply the distance measurement and input the measurement into the appropriate conversion mathematics in order to output a volumetric measurement of fluid drawn in by the syringe.

In some aspects, microprocessor 184 can transmit the volumetric measurement to a local storage and/or recording device 196. Exemplary data storage may include non-transitory computer readable media, such as flash memory, random access memory, or other storage devices. For example, where there is no wireless connection, battery is low, etc., device 100 can temporarily store measurement records in local database 196. In some aspects, data storage may be external.

In some aspects, microprocessor 184 can also transmit the volumetric measurement for display at user interface 122. User interface 122 can comprise a display 124 on which the volumetric measurement can be displayed. Display 124 can be a digital display that can be configured to display syringe size, volume of fluid that has been collected or expelled, a saved measurement if device 100 has been locked, an indicator for measurement repeating mode, a state of a wireless connection, and remaining battery life. Other information can also be displayed on display 124 relevant to use of device 100. In some aspects, display 124 can be disposed adjacent to plurality of buttons and/or switches 122A-E for quick visual reference of any selections made by user interaction with buttons 122A-E.

In some aspects, microprocessor can also transmit the volumetric measurement to a wireless transmitter or communicator 192 and a wireless connector 194 stored in a housing 190 of device 100. Transmitter 192 can be functionally connected with a wireless connector 194, which can relay data (e.g., stored measurements) to an electronic interface of a server 402 that is configured to store electronic medical records and/or verify dosage amounts.

Once the volumetric measurement has been transmitted to server 402, server 402 can store electronic medical records and/or verify dosage amounts. This information can then be used to provide a feedback mechanism for ensuring that the right dosage and medication was made. The information my also be used for tracking what medication was given to a patient by a specific user. In addition, it can accurately bill the patient for the exact medication received by the patient and allow for the ability to determine which patient got which medication, if needed during a recall of the medication. Server 402 can comprise any server, node, computer, or unit that is configured to store electronic medical records, verify dosage amounts, track medication, bill the patient, etc. Server 402 may include at least one processor (not shown), and modules (not shown) configured to store electronic medical records, verify dosage amounts, track medication, bill the patient, etc. In some aspects, the processor of server 402 may include a microprocessor, a central processing unit (CPU), or any other like hardware-based processor unit that is configured to execute and/or utilize the modules of server 402 (e.g., a software based algorithm). In some embodiments, the modules of server 402 may be stored in memory (not shown), such as random access memory (RAM), read only memory (ROM), optical read/write memory, cache memory, magnetic read/write memory, flash memory, or any other non-transitory storage media.

Figure 9:
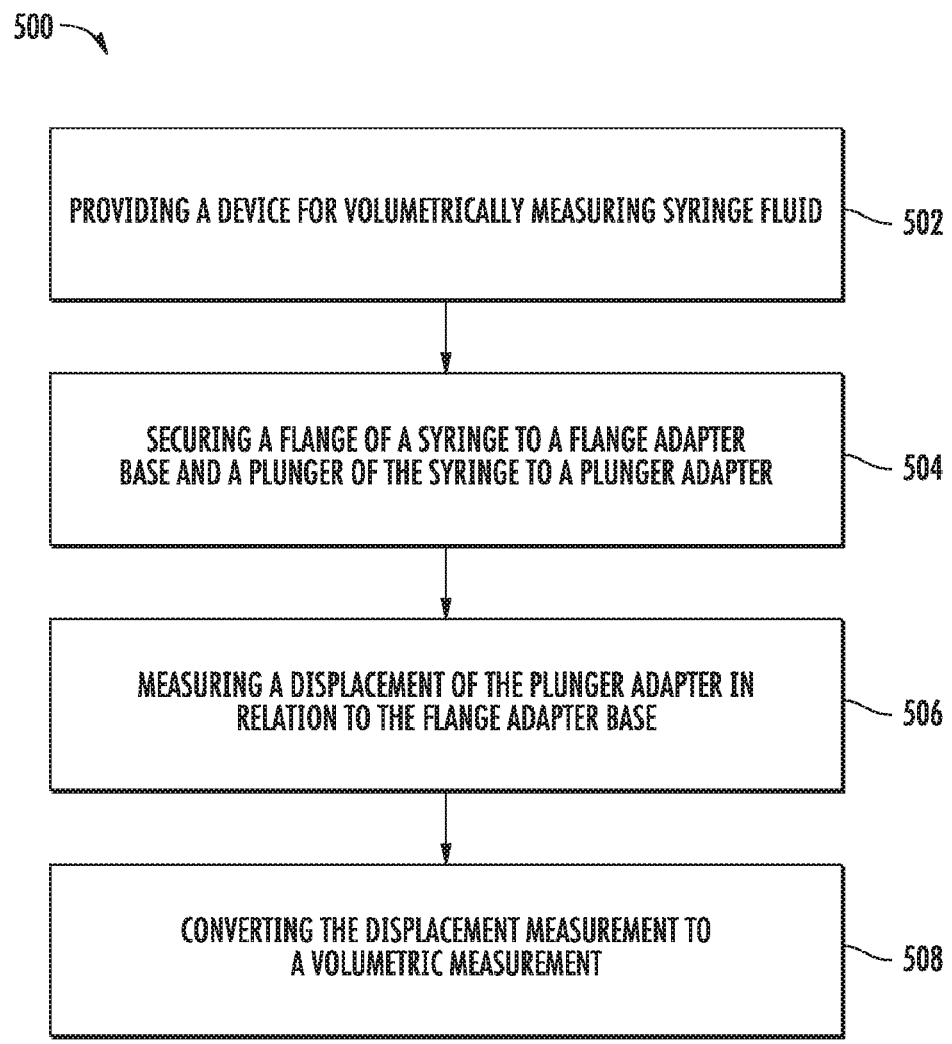
FIG. 9 is a flow diagram of an exemplary method for volumetrically measuring syringe fluid according to some embodiments of the subject matter described herein.

FIG. 9 is a flow chart depicting an exemplary method, generally designated 500, for volumetrically measuring syringe fluid according to an embodiment of the subject matter described herein.

Referring to FIG. 9, in block 502, a device 100 for volumetrically measuring syringe fluid is provided. In some aspects, device 100 can comprise a reference plate 140, a flange adapter base 110 attached at a first end of reference plate 140 for receiving a flange 220 of a syringe 200, a plunger adapter 130 configured to slidingly move along a length of reference plate 140 and disposed adjacent to a housing 120 for receiving a plunger 210 of syringe 200, a displacement sensor 172 disposed in housing 120 and configured to measure a displacement Δx of plunger adapter 130 in relation to flange adapter base 110 as plunger adapter 130 is slid along the length of reference plate 140, and a displacement conversion mechanism 184 disposed in housing 120 and configured to convert displacement Δx of plunger adapter 130 to a volumetric measurement in order to determine a volume of fluid syringe 200 has drawn in.

In some aspects, displacement sensor 172 can comprise at least one of: a capacitive sensor; a laser sensor, a drop line sensor, an inductive sensor, a rod capacitive sensor, a sonic sensor, a linear variable differential transformer (LVDT) with distance measurement points attached to plunger adapter 130 and flange adapter base 110, or any combination thereof.

In some aspects, a user interface 122 can be disposed on a top surface of housing 120 of device 100. User interface 122 can comprise functionality including, for example, at least one of selecting a size of the syringe, zeroing the device, activating and deactivating a measurement repetition mode, mechanically locking motion of the device and saving the displacement measurement, and/or transmitting the displacement measurement.

In some aspects, flange adapter base 110 and/or the plunger adapter 130 can be configured to resiliently receive syringes sized approximately between 1 mL and 60 mL.

In block 504, flange 220 of syringe 200 can be secured to flange adapter base 110 and plunger 210 of syringe 200 can be secured to plunger adapter 130.

In block 506, displacement Δx of plunger adapter 130 in relation to flange adapter base 110 can be measured. For example, as plunger adapter 130 is slidingly moved along the length of reference plate 140, displacement sensor 172 can measure displacement Δx.

In block 508, displacement measurement Δx can be converted to a volumetric measurement. For example, displacement conversion mechanism 184 can use conversion mathematics to convert displacement measurement Δx to a volumetric measurement.

In some aspects, a calibration function corresponding to a size of syringe 200 for converting displacement measurement Δx of plunger adapter 130 to the volumetric measurement can be applied.

In some aspects, method 500 can transmit the volumetric measurement to at least one of a display 124 on the device, a storage database 196, and a server 402.

In some aspects, method 500 can automatically repeat, by the measurement repetition mode, volume measurements by storing the volumetric measurement, disengaging a clamping mechanism 126 disposed in housing 120, where the clamping mechanism 126 can be for preventing sliding movement of plunger adapter 130 along the length of reference plate 140, zeroing device 100, and automatically reengaging clamping mechanism 126 when at least one subsequent volumetric measurement is equal to the previously stored volumetric measurement.

In some aspects, method 500 determines the volumetric measurement of the volume of fluid syringe 200 has drawn in is at least approximately ±0.3% accurate.

It will be appreciated that exemplary process 500 is for illustrative purposes and that different and/or additional actions may be used. It will also be appreciated that various actions described herein may occur in a different order or sequence.

Accordingly, while the devices, systems, and methods have been described herein in reference to specific embodiments, features, and illustrative embodiments, it will be appreciated that the utility of the subject matter is not thus limited, but rather extends to and encompasses numerous other variations, modifications and alternative embodiments, as will suggest themselves to those of ordinary skill in the field of the present subject matter, based on the disclosure herein.

Various combinations and sub-combinations of the structures and features described herein are contemplated and will be apparent to a skilled person having knowledge of this disclosure. Any of the various features and elements as disclosed herein may be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims. It is understood that various details of the presently disclosed subject matter may be changed without departing from the scope of the presently disclosed subject matter. Furthermore, the foregoing description is for the purpose of illustration only, and not for the purpose of limitation.

What is claimed is:

1. A device for volumetrically measuring syringe fluid, the device comprising: a reference plate; a flange adapter base attached at a first end of the reference plate for receiving a flange of a syringe; a plunger adapter attached to a housing for receiving a plunger of the syringe, the plunger adapter and the housing being configured to slidingly move along a length of the reference plate; a displacement sensor disposed in the housing and configured to measure a displacement of the plunger adapter in relation to the flange adapter base as the plunger adapter along with the housing are slid along the length of the reference plate; and a displacement conversion mechanism disposed in the housing and configured to convert the displacement measurement of the plunger adapter to a volumetric measurement in order to determine a volume of fluid the syringe has drawn in.

2. The device of claim 1, wherein the device is configured to determine the volumetric measurement of the volume of fluid the syringe has drawn in to at least approximately ±0.3% accuracy.

3. The device of claim 1, wherein the displacement sensor comprises at least one of a capacitive sensor; a laser sensor, a drop line sensor, an inductive sensor, a rod capacitive sensor, a sonic sensor, a linear variable differential transformer (LVDT) with distance measurement points attached to the plunger adapter and the flange adapter base, or any combination thereof.

4. The device of claim 1, wherein the device is configured to transmit volumetric measurement to at least one of a display on the device, a storage database, and a server.

5. The device of claim 1, further comprising a user interface disposed on a top surface of the housing of the device, the user interface comprising functionality including at least one of selecting a size of the syringe, zeroing the device, activating and deactivating a measurement repetition mode, mechanically locking motion of the device and saving the displacement measurement, and/or transmitting the displacement measurement.

6. The device of claim 5, wherein the measurement repetition mode is configured to automatically repeat volume measurements by storing the volumetric measurement, disengaging a clamping mechanism disposed in the housing, the clamping mechanism for preventing sliding movement of the plunger adapter along the length of the reference plate, zeroing the device, and automatically reengaging the clamping mechanism when at least one subsequent volumetric measurement is equal to the previously stored volumetric measurement.

7. The device of claim 1, wherein the displacement conversion mechanism is configured to apply a calibration function or coefficient corresponding to a size of the syringe to convert the displacement measurement of the plunger adapter to the volumetric measurement.

8. The device of claim 1, wherein the flange adapter base and/or the plunger adapter are configured to resiliently receive syringes sized from 1 mL to 60 mL.

9. A system for volumetrically measuring syringe fluid, the system comprising: a device comprising: a reference plate, a flange adapter base attached at a first end of the reference plate for receiving a flange of a syringe, a plunger adapter attached to a housing for receiving a plunger of the syringe, the plunger adapter and the housing being configured to slidingly move along a length of the reference plate, a displacement sensor disposed in the housing and configured to measure a displacement of the plunger adapter in relation to the flange adapter base as the plunger adapter along with the housing are slid along the length of the reference plate, and a displacement conversion mechanism disposed in the housing and configured to convert the displacement measurement of the plunger adapter to a volumetric measurement in order to determine a volume of fluid the syringe has drawn in; and a server connected with the device.

10. The system of claim 9, wherein the device is configured to determine the volumetric measurement of the volume of fluid the syringe has drawn in to at least approximately ±0.3% accuracy.

11. The system of claim 9, wherein the displacement sensor comprises at least one of: a capacitive sensor; a laser sensor, a drop line sensor, an inductive sensor, a rod capacitive sensor, a sonic sensor, a linear variable differential transformer (LVDT) with distance measurement points attached to the plunger adapter and the flange adapter base, or any combination thereof.

12. The system of claim 9, wherein the device is configured to transmit the volumetric measurement to at least one of a display on the device, a storage database, and the server.

13. The system of claim 9, further comprising a user interface disposed on a surface of the housing of the device, the user interface comprising functionality including at least one of selecting a size of the syringe, zeroing the device, activating and deactivating a measurement repetition mode, mechanically locking motion of the device and saving the displacement measurement, and/or transmitting the displacement measurement.

14. The system of claim 13, wherein the measurement repetition mode is configured to automatically repeat volume measurements by storing the volumetric measurement, disengaging a clamping mechanism disposed in the housing, the clamping mechanism for preventing sliding movement of the plunger adapter along the length of the reference plate, zeroing the device, and automatically reengaging the clamping mechanism when at least one subsequent volumetric measurement is equal to the previously stored volumetric measurement.

15. The system of claim 9, wherein the displacement conversion mechanism is configured to apply a calibration function or coefficient corresponding to a size of the syringe to convert the displacement measurement of the plunger adapter to the volumetric measurement.

16. The system of claim 9, wherein the flange adapter base and/or the plunger adapter are configured to resiliently receive syringes sized from 1 mL to 60 mL.

17. A method for volumetrically measuring syringe fluid, the method comprising: providing a device comprising a reference plate, a flange adapter base attached at a first end of the reference plate for receiving a flange of a syringe, a plunger adapter attached to a housing for receiving a plunger of the syringe, the plunger adapter and the housing being configured to slidingly move along a length of the reference plate, a displacement sensor disposed in the housing, and a displacement conversion mechanism disposed in the housing; securing the flange of the syringe to the flange adapter base and the plunger of the syringe to the plunger adapter; measuring, by the displacement sensor, a displacement of the plunger adapter in relation to the flange adapter base, as the plunger adapter along with the housing are slidingly moved along the length of the reference plate; and converting, by the displacement conversion mechanism, the displacement measurement of the plunger adapter to a volumetric measurement in order to determine a volume of fluid the syringe has drawn in.

18. The method of claim 17, further comprising interfacing with a user interface disposed on a top surface of the housing of the device, the interface comprising functionality including at least one of selecting a size of the syringe, zeroing the device, activating and deactivating a measurement repetition mode, mechanically locking motion of the device and saving the displacement measurement, and transmitting the displacement measurement.

19. The method of claim 18, further comprising automatically repeating, by the measurement repetition mode, volume measurements by storing the volumetric measurement, disengaging a clamping mechanism disposed in the housing, the clamping mechanism for preventing sliding movement of the plunger adapter along the length of the reference plate, zeroing the device, and automatically reengaging the clamping mechanism when at least one subsequent volumetric measurement is equal to the previously stored volumetric measurement.

20. The method of claim 17, further comprising applying a calibration function or coefficient corresponding to a size of the syringe for converting the displacement measurement of the plunger adapter to the volumetric measurement.

21. The method of claim 17, further comprising transmitting the volumetric measurement to at least one of a display on the device, a storage database, and a server.

22. The method of claim 17, wherein the volumetric measurement of the volume of fluid the syringe has drawn in is at least approximately ±0.3% accurate.

23. The method of claim 17, wherein the flange adapter base and/or the plunger adapter of the device are configured to resiliently receive syringes sized from 1 mL to 60 mL.

24. The method of claim 17, wherein the displacement sensor of the device comprises at least one of: a capacitive sensor; a laser sensor, a drop line sensor, an inductive sensor, a rod capacitive sensor, a sonic sensor, a linear variable differential transformer (LVDT) with distance measurement points attached to the plunger adapter and the flange adapter base, or any combination thereof.

* * * * *